United States Patent
Han et al.

(10) Patent No.: US 8,702,632 B2
(45) Date of Patent: Apr. 22, 2014

(54) WEARABLE ROBOT FOR ASSISTING MUSCULAR STRENGTH OF LOWER EXTREMITY

(75) Inventors: Chang-Soo Han, Seoul (KR); Jung-Soo Han, Seoul (KR); Jae-Ho Jang, Gyeonggi-do (KR); Seung-Nam Yu, Gyeonggi-do (KR); Hee-Don Lee, Gyeonggi-do (KR); Seung-Hoon Lee, Seoul (KR); Wan-Soo Kim, Gyeonggi-do (KR)

(73) Assignee: IUCF-HYU (Industry-University Cooperation Foundation Hanyang University), Seoul (KR)

( * ) Notice: Subject to any disclaimer, the term of this patent is extended or adjusted under 35 U.S.C. 154(b) by 453 days.

(21) Appl. No.: 13/143,759

(22) PCT Filed: Feb. 27, 2009

(86) PCT No.: PCT/KR2009/000939
§ 371 (c)(1),
(2), (4) Date: Jul. 8, 2011

(87) PCT Pub. No.: WO2010/079862
PCT Pub. Date: Jul. 15, 2010

(65) Prior Publication Data
US 2011/0264016 A1  Oct. 27, 2011

(30) Foreign Application Priority Data
Jan. 12, 2009  (KR) .................. 10-2009-0002321

(51) Int. Cl.
*A61H 1/02* (2006.01)
*A61H 3/00* (2006.01)

(52) U.S. Cl.
USPC ......... 601/35; 601/5; 601/23; 602/16; 602/23

(58) Field of Classification Search
USPC .............. 601/5, 23, 33, 34, 35, 84, 86, 90, 98
See application file for complete search history.

(56) References Cited

U.S. PATENT DOCUMENTS

| 7,462,159 | B1 | 12/2008 | Shlomovitz et al. | ............ 602/16 |
| 7,628,766 | B1 * | 12/2009 | Kazerooni et al. | ............ 601/35 |
| 2006/0276728 | A1 * | 12/2006 | Ashihara et al. | .................. 601/5 |

FOREIGN PATENT DOCUMENTS

| JP | 2005230099 | 9/2005 |
| WO | WO 9501141 | 1/1995 |
| WO | WO 2008036746 | 3/2008 |

OTHER PUBLICATIONS

International Search Report dated Oct. 5, 2009 for International Application No. PCT/KR2009/000939, filed Feb. 27, 2009.
Written Opinion dated Oct. 5, 2009 from International Application No. PCT/KR2009/000939, filed Feb. 27, 2009.

* cited by examiner

*Primary Examiner* — Quang D Thanh
(74) *Attorney, Agent, or Firm* — Brian R. Morrison; Westman, Champlin & Koehler, P.A.

(57) ABSTRACT

A wearable robot for assisting muscular strength of the lower extremity of a user: The wearable robot can be worn on user's legs and includes a central securing part, a hip joint part hingably coupled to either side of a lower end of the central securing part, a femur part fastened to the hip joint part and having rigidity, a knee part including an outer frame and a knee assistant, and a drive unit fastened to one of the hip joint part and the knee joint part to allow operation of the joint part. The outer frame includes an upper side outer frame fastened to a lower end of the femur part and a lower side outer frame fastened to the upper side outer frame by a rotatable knee joint part Both the upper side outer frame and the lower side outer frame are fastened to the knee assistant worn by the user.

8 Claims, 2 Drawing Sheets

WEARABLE ROBOT FOR ASSISTING MUSCULAR STRENGTH OF LOWER EXTREMITY

CROSS-REFERENCE TO RELATED APPLICATION(S)

This Application is a 371 National Stage Application of International Application No. PCT/KR2009/000939, filed on Feb. 27, 2009, published as International Publication No. WO 2010/079862 A1, and which claims priority to Korean Patent Application No. 10-2009-0002321, filed on Jan. 12, 2009.

TECHNICAL FIELD

The present invention relates to a robot for assisting muscular strength of a user and, more particularly, to a wearable robot for assisting muscular strength of the lower extremity of a user.

BACKGROUND ART

In general, a wearable robot for assisting muscular strength of the lower extremity refers to a robot that is developed based on humanrobot synchronization to be worn by a user to help waking of the user by assisting the strength of the user's legs.

Although such a wearable robot for assisting the muscular strength of the lower extremity originates from rehabilitation assistants for degenerative muscular disease patients, there are many attempts in recent years to apply the wearable robot to muscular strength assistants for the elderly, soldiers wearing battle equipment, workers carrying heavy loads in work sites, surgical patients, medical patients undergoing longterm hospitalization, and the like.

As a result, various wearable robots usually worn around the knee joint of a user have been developed to assist the muscular strength of degenerative muscular disease patients or the elderly. However, wearable robots for work sites or the like have yet to be realized in practice.

For use in work sites, the wearable robot for assisting the lower extremity must be used along with a robot for assisting muscular strength of a user's upper body, or must overcome problems relating to load exerted on the lower extremity of the user since a high load is generally exerted on the user and the robot when the user wearing the wearable robot carries the high load.

Further, when all joint parts of the wearable robot are active joints including drive units as in a leg of a general robot, the driver units cause an excessive increase in weight of the wearable robot and complicate the configuration thereof, thereby causing frequent malfunction.

DISCLOSURE OF INVENTION

Technical Problem

The present invention is conceived to solve the problems as described above, and an aspect of the present invention is to provide a wearable robot for assisting muscular strength of the lower extremity, which has a reduced weight and a simple structure, and allows a user wearing the robot to experience a reduced load when carrying a high load.

Technical Solution

According to an aspect of the present invention, a wearable robot for assisting muscular strength of the lower extremity worn on legs of a user includes: a central securing part; a hip joint part hingably coupled to either side of a lower end of the central securing part; a femur part fastened to the hip joint part and having rigidity; a knee part including an outer frame and a knee assistant, the outer frame including an upper-side outer frame fastened to a lower end of the femur part and a lower-side outer frame fastened to the upper-side outer frame by a rotatable knee joint part, both the upper-side outer frame and the lower-side outer frame being fastened to the knee assistant worn by the user; and a drive unit fastened to one of the hip joint part and the knee joint part to allow operation of the joint part fastened to the drive unit.

The wearable robot may further include an ankle part fastened to a lower end of the lower-side outer frame and placed on the user s ankle, the ankle part being provided with a bottom member contacting a foot sole of the user and connected to the ankle part by an elastic support member to transfer a weight of the robot and an added weight to the ground such that a reduced weight can be applied to the lower extremity of the user.

The components of the wearable robot from the central securing part to the bottom member may be fastened to one another through fastening members having rigidity to transfer the weight of the robot and an added weight to the ground, whereby a user does not suffer a burden of the weights.

The central securing part may include an upper body wearing portion having a shoulder strap to be worn by the user, and a coupling portion fastened to the upper body wearing portion and provided at a lower end thereof with the hip joint part.

The drive unit may be fastened to the knee joint part to rotate the upper-side outer frame and the lower-side outer frame, and the femur part may have elasticity and may be a four-bar linkage including a spring damper.

The knee joint part may be provided with a harmonic drive reduction gear.

The drive unit may be fastened to the hip joint part to allow hinge operation of the hip joint part, and the knee joint part may be provided with an elastic rotational member connected to the upper-side outer frame and the lower-side outer frame.

Advantageous Effects

In the wearable robot according to the embodiments of the present invention, the drive unit is provided only to one of the hip joint part and the knee joint part, and the elastic member is added to the robot to assist another joint, thereby allowing the user wearing the wearable robot to walk only with a single active joint.

As such, according to the embodiments of the present invention, the wearable robot for assisting the muscular strength of the lower extremity transfers the weight of the robot and an added weight to the ground via a structure for distributing the weight and connecting the components of the robot to one another, so that a significantly reduced weight can be applied to the user wearing the wearable robot.

Further, the wearable robot minimizes the use of a drive unit by employing a passive joint, thereby reducing the weight of the robot and malfunction frequency.

Furthermore, the wearable robot has a reduced number of drivers, so that the number of layers for control and calculation logics is reduced, thereby preventing system malfunction.

BRIEF DESCRIPTION OF DRAWINGS

The above and other aspects, features and advantages of the present invention will be more clearly understood from the following description taken in conjunction with the accompanying drawings, in which.

BEST MODE FOR CARRYING OUT THE INVENTION

Figure 1:
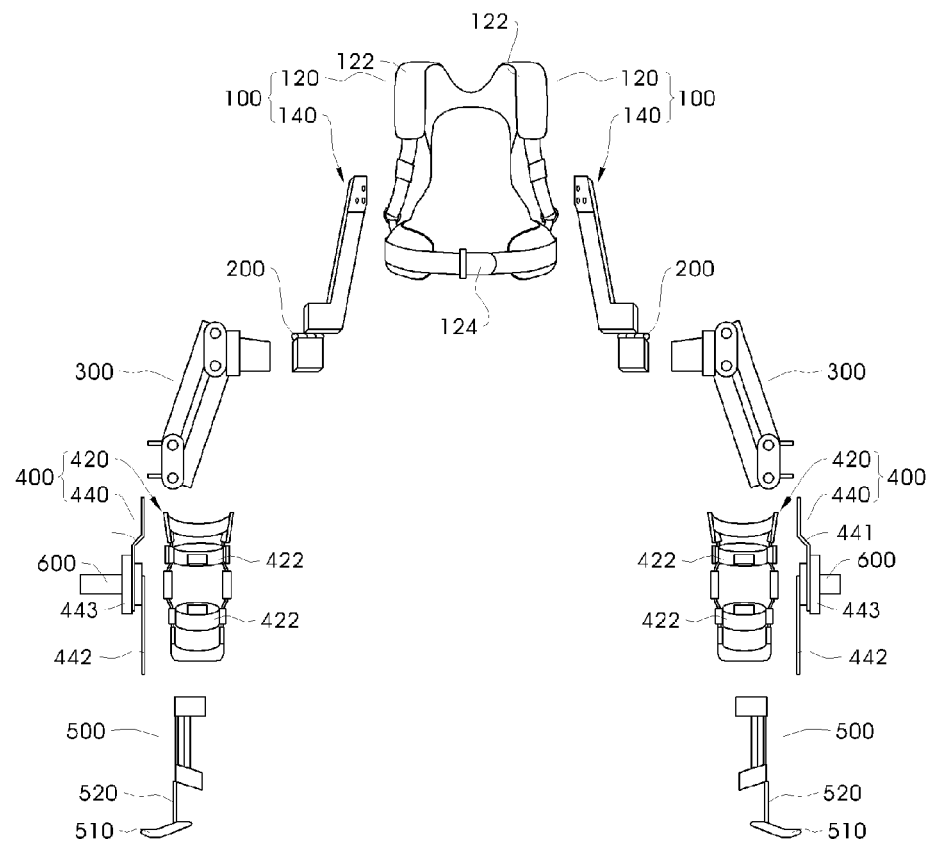
FIG. 1 is a view of a wearable robot for assisting muscular strength of the lower extremity according to an embodiment of the present invention.

Exemplary embodiments of the present invention will be described in detail with reference to the accompanying drawings, through which like elements will be denoted by like reference numerals.

FIG. 1 is a view of a wearable robot for assisting muscular strength of the lower extremity according to an embodiment of the present invention. In the wearable robot of this embodiment shown in FIG. 1, a drive unit 600 is provided only to a knee joint part 443 to rotate an upperside outer frame 441 and a lowerside outer frame 442, and thus, a hip joint part 200 is constituted by a passive joint to which such a drive unit is not provided.

In FIG. 1, the wearable robot includes a central securing part 100, the hip joint part 200, a femur part 300, a knee part 400, and an ankle part 500.

The central securing part 100 serves to bridge right and left parts of the wearable robot to each other such that the right and left parts of the wearable robot can be integrally put on the legs of a user, respectively. In order to allow load to be exerted not on the user's body but on the wearable robot for assisting the muscular strength of the lower extremity when the wearable robot is fastened to a robot component for assisting muscular strength of an upper body of the user or is used to carry a freight of a heavy weight, the wearable robot is configured to allow the load to be exerted on the central securing part 100.

The central securing part 100 may have various configurations. For example, the central securing part 100 may include an upper body wearing portion 120 and coupling members 140. The upper body wearing portion 120 is provided with a shoulder strap 122, which allows the upper body wearing portion 120 to be carried on the user's upper body like a backpack. The upper body wearing portion 120 may further include a belt 124 to improve stability of the robot. Although it is not desirable to fabricate the upper body wearing portion 120 with a rigid material, the coupling members 140 made of a rigid material are fastened to the upper body wearing portion 120 since the central securing part 100 requires a rigid portion for its application. Each of the coupling members 140 may be made of a steel plate in an elongated shape for load distribution, and are longitudinally fastened to the rear side of the upper body wearing portion 120.

The hip joint part 200 is a hinge connector disposed between the central securing part 100 and the femur part 300, and acts like a human hip joint. The hip joint part 200 is provided to either side of a lower end of the central securing part 100 and is also fastened to the femur part 300. The hip joint part 200 may be provided to each lower end of the coupling members 140, which are made of the elongated steel plate.

The femur part 300 connects the hip joint part 200 to the knee part 400 and has sufficient rigidity to allow the femur part 300 to endure load exerted on the central securing part 100. In the wearable robot according to this embodiment, since the hip joint part 200 is constituted by a passive joint, the femur part 300 with elasticity is connected to the hip joint part 200 to assist motion of the hip joint part 200, which is not provided with the drive unit, through the elasticity of the femur part 300. Further, the load applied to the central securing part 100 is distributed by the elasticity of the femur part 300, thereby relieving impact that can be imposed on the robot when a user wearing the robot walks. The femur part 300 may be realized in various forms. For example, the femur part 300 may be a fourbar linkage that includes a suitable adjusted spring damper. In this case, the femur part 300 has a suitable rigidity and exhibits superior effect in distribution of load while assisting hinge operation of the hip joint part 200.

The knee part 400 includes a knee assistant 420 and an outer frame 440. The knee assistant 420 is directly placed on the user's body and is configured to be located over upper and lower parts of the knee of the user. The knee assistant 420 is provided with wearing members 422 to secure the knee assistant 420 to the user's body when the knee assistant 420 is placed on the user's body. At least one wearing member 422 may be provided to each of the upper and lower parts of the knee. Alternatively, a plurality of wearing members 422 may be provided thereto. The outer frame 440 is fastened to the knee assistant 420, and is located outside the user's leg.

The outer frame 440 includes an upperside outer frame 441 and a lowerside outer frame 442 joined to each other via a rotatable knee joint part 443. The knee joint part 443 is located beside the knee, the upperside outer frame 441 is located above the knee, and the lowerside outer frame 442 is located below the knee. At this time, an upper end of the upperside outer frame 441 is fastened to a lower end of the femur part 300. The outer frame 440 may be formed in a plate or bar shape, but the present invention is not limited thereto.

The knee joint part 443 includes a gear. Advantageously, a reduction gear may be provided to the knee joint part 443 in order to reduce backlash of a general gear. To this end, harmonic drive may be used for the knee joint part 443 due to superior efficiency thereof.

Figure 2:
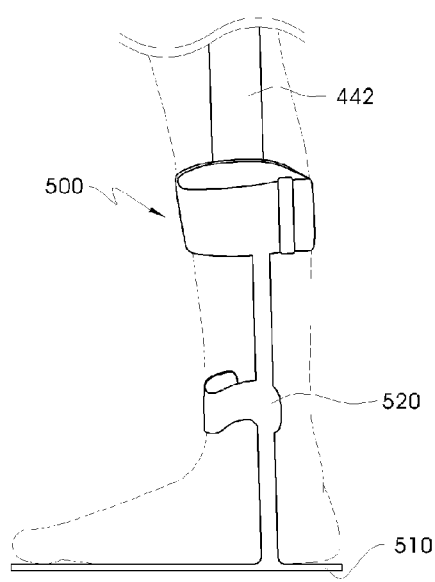
FIG. 2 is a view of an ankle part of the wearable robot according to the embodiment of the present invention.

The ankle part 500 is put on the user's ankle and has an upper end fastened to the lower end of the lowerside outer frame 442. FIG. 2 shows the ankle part of the wearable robot according to the embodiment of the invention. The ankle part 500 is provided with a bottom member 510 contacting a user's foot sole and the ground. The load of the robot and the load exerted on the central securing part 100 are distributed through the femur part 300, the outer frame 440 and the ankle part 500 while being transferred to the ground through the bottom member 510, so that a significantly reduced load can be applied to the user's lower extremity.

Although an articulation is also located in the ankle on which the ankle part 500 is placed, the ankle part 500 is not provided with the drive unit and is connected to the bottom member 510 through an elastic support member 520. When pressure of the foot sole applied to the bottom member 510 is varied by bending the ankle articulation, the support member 520 is elastically deformed so as to act as an ankle articulation part. Particularly, the support member 520 helps a user wearing the wearable robot to walk by storing and releasing elastic energy through elastic deformation.

The wearable robot according to this embodiment also includes a sensor and a controller to operate the drive unit 600, which are known in the art, and a detailed description thereof will be omitted herein.

Figure 3:
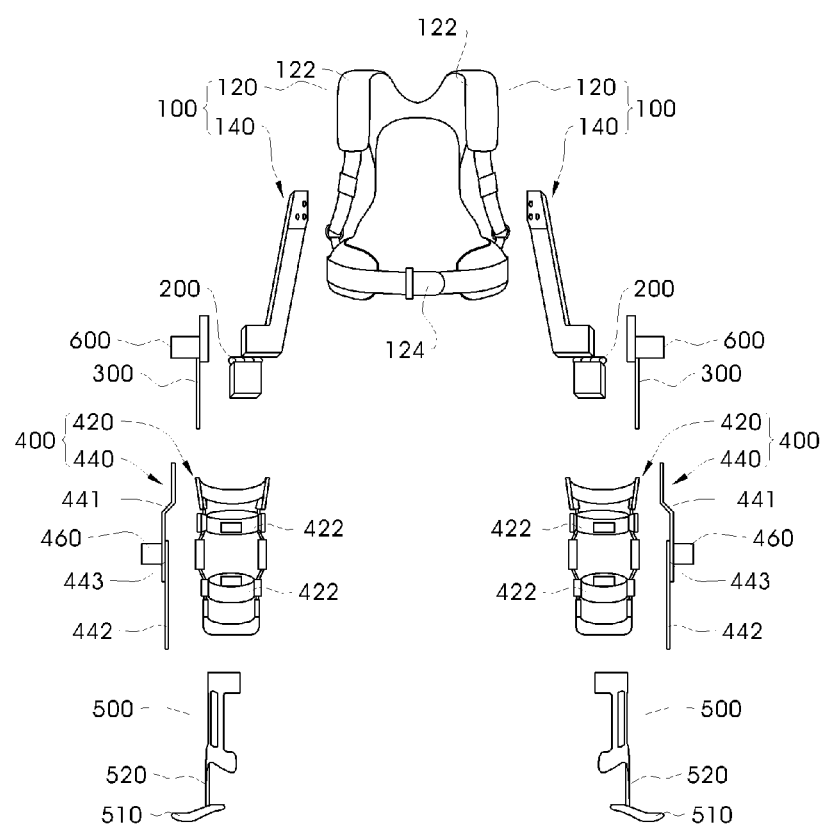
FIG. 3 is a view of a wearable robot for assisting muscular strength of the lower extremity according to another embodiment of the present invention.

FIG. 3 is a view of a wearable robot for assisting muscular strength of the lower extremity according to another embodiment of the present invention. In the wearable robot of this embodiment shown in FIG. 3, a drive unit 600 is provided only to a hip joint part 200 to allow hinge operation thereof, and thus, a knee joint part 443 is constituted by a passive joint to which such a drive unit is not provided.

In FIG. 3, the wearable robot includes a central securing part 100, the hip joint part 200, a femur part 300, a knee part 400, and an ankle part 500.

A description of the same components as that of the above embodiment will be omitted herein.

In this embodiment where the drive unit 600 is provided only to the hip joint part 200, there is no need to assist the hinge operation of the hip joint part 200 with elasticity of the femur part 300. Therefore, the femur part 300 may have a simple, rigid configuration.

In this embodiment, although the knee part 400 is provided with an outer frame 440 to allow motion of the body while distributing load, the knee joint part 443 is not provided with the drive unit. Here, an elastic rotational member 460 is provided to the knee joint part 443. The elastic rotational member 460 may be an elastic member using a coil spring.

The wearable robot according to this embodiment also includes a sensor and a controller to operate the drive unit 600, which are known in the art, and a detailed description thereof will be omitted herein.

As apparent from the above description, in the wearable robot for assisting the muscular strength of the lower extremity according to the embodiments of the invention, a drive unit is provided only to one of a knee joint part and a hip joint part of the robot, and an elastic member is added to the robot for assistant of another joint. As a result, the wearable robot according to the embodiments of the invention has the following effects in view of materialization, distribution, and commercial availability of the robot. First, the wearable robot enables cost reduction in development and manufacture of a system. Secondly, the wearable robot has a reduced number of drive units, and allows easy and efficient control and calculation of the system through positional variation of the drive unit.

Further, in the wearable robot according to the embodiments of the invention, the number of layers for control and calculation logics is reduced, thereby preventing malfunction of the system while improving reliability of the system.

Although the present invention has been described with reference to the embodiments and the accompanying drawings, it will be apparent to a person having ordinary knowledge in the art that this invention is not limited to the embodiments, and that various modifications, changes and substitutions can be made without departing from the spirit and scope of the present invention. Accordingly, the scope of the present invention should be limited only by the accompanying claims.

The invention claimed is:

1. A wearable robot for assisting muscular strength of the lower extremity worn on the user's legs, comprising:
   a central securing part;
   a hip joint part hingably coupled to either side of a lower end of the central securing part;
   a femur part fastened to the hip joint part and having rigidity;
   a knee part comprising an outer frame and a knee assistant, the outer frame including an upperside outer frame fastened to a lower end of the femur part and a lowerside outer frame fastened to the upperside outer frame by a rotatable knee joint part, both the upperside outer frame and the lowerside outer frame being fastened to the knee assistant worn by the user; and
   a drive unit fastened to one of the hip joint part and the knee joint part to allow operation of the joint part fastened to the drive unit.

2. The wearable robot according to claim 1, further comprising:
   an ankle part fastened to a lower end of the lowerside outer frame and placed on the user's ankle, the ankle part being provided with a bottom member contacting a foot sole of the user to transfer a weight of the robot and a weight of a freight carried by the user wearing the wearable robot to the ground such that a reduced weight can be applied to the lower extremity of the user.

3. The wearable robot according to claim 2, wherein the bottom member is connected to the ankle part by an elastic support member.

4. The wearable robot according to claim 1, wherein the central securing part comprises an upper body wearing portion having a shoulder strap to be worn by the user, and a coupling portion fastened to the upper body wearing portion and provided at a lower end thereof with the hip joint part.

5. The wearable robot according to claim 1, wherein the drive unit is fastened to the knee joint part to rotate the upperside outer frame and the lowerside outer frame, and the femur part has elasticity.

6. The wearable robot according to claim 5, wherein the femur part is a fourbar linkage including a spring damper.

7. The wearable robot according to claim 5, wherein the knee joint part is provided with a harmonic drive reduction gear.

8. The wearable robot according to claim 1, wherein the drive unit is fastened to the hip joint part to allow hinge operation of the hip joint part, and the knee joint part is provided with an elastic rotational member connected to the upper-side outer frame and the lower-side outer frame.

* * * * *